United States Patent
Sun et al.

(10) Patent No.: US 7,271,120 B2
(45) Date of Patent: Sep. 18, 2007

(54) CATALYST FOR THE SYNTHESIS OF DIMETHYL CARBONATE FROM UREA AND METHANOL, PREPARATION AND USE THEREOF

(75) Inventors: Yuhan Sun, Taiyuan (CN); Wei Wei, Taiyuan (CN); Ning Zhao, Taiyuan (CN); Baoyuan Sun, Shandong (CN); Bingsheng Zhang, Shandong (CN); Yanjun Chen, Shandong (CN)

(73) Assignees: Institute of Coal Chemistry, Chinese Academy of Sciences, Taiyuan (CN); Feicheng Acid Chemicals Co., Ltd., Shandong (CN)

( * ) Notice: Subject to any disclaimer, the term of this patent is extended or adjusted under 35 U.S.C. 154(b) by 0 days.

(21) Appl. No.: 11/209,052

(22) Filed: Aug. 22, 2005

(65) Prior Publication Data

US 2006/0047136 A1    Mar. 2, 2006

(30) Foreign Application Priority Data

Aug. 27, 2004    (CN)   ...................... 2004 1 00125041

(51) Int. Cl.
*B01J 31/02* (2006.01)
*B01J 371/10* (2006.01)
*B01J 6/00* (2006.01)

(52) U.S. Cl. ...................... 502/158; 502/329; 502/224; 502/226; 502/342; 502/104; 502/107; 502/113; 502/115; 502/116; 502/133; 502/134; 502/151; 502/178; 502/181; 502/182; 502/183; 502/184; 502/304; 502/324; 502/328

(58) Field of Classification Search ................ 558/277; 502/63, 84, 158, 329, 104, 107, 113, 115, 502/116, 133, 134, 151, 178, 181, 182, 304, 502/324

See application file for complete search history.

(56) References Cited

U.S. PATENT DOCUMENTS 4,900,705 A * 2/1990 Sawicki et al. ............. 502/158
5,436,362 A * 7/1995 Kondoh et al. ............. 558/277

FOREIGN PATENT DOCUMENTS

EP           478073      *   9/1991

* cited by examiner

*Primary Examiner*—Rebecca Anderson
*Assistant Examiner*—Yong Chu
(74) *Attorney, Agent, or Firm*—Hunton & Williams LLP

(57) ABSTRACT

A catalyst for the preparation of dimethyl carbonate from urea and methanol having a composition on weight base of: active component of from 20 to 50 wt %, and carrier of from 80 to 50 wt %, and prepared by equal-volume spraying and impregnating method is disclosed. The method for the synthesis of dimethyl carbonate can be carried out in a catalytic rectification reactor, said method comprising: (1) dissolving urea in methanol to form a methanol solution of urea; and (2) feeding the methanol solution of urea and methanol counter-currently into the reaction zone, wherein the reaction is carried out at conditions including reaction temperature of from 120° C. to 250° C., reaction pressure of from 0.1 MPa to 5 MPa, kettle bottom temperature of from 70° C. to 210° C., stripping section temperature of from 70° C. to 250° C., rectifying section temperature of from 70° C. to 280° C., and reflux ratio of from 1:1 to 20:1. The preparation of the catalyst according to the present invention is simple and has good repeatability, and the catalyst could further enhance the yield of DMC as well as conversion of urea in the catalytic rectification reactor.

5 Claims, No Drawings

CATALYST FOR THE SYNTHESIS OF DIMETHYL CARBONATE FROM UREA AND METHANOL, PREPARATION AND USE THEREOF

TECHNICAL FIELD

The present invention relates to a catalyst and a method for preparing the same, more particularly, to a supported catalyst for direct synthesis of dimethyl carbonate from urea and methanol, to a method for preparing the same, and to use thereof.

BACKGROUND ART

Dimethyl carbonate (DMC) is a novel "green" chemical product to which great attention is paid both domestically and internationally. Since DMC comprises methoxy group, carbonyl group and carbonyl methyl oxygen group in a molecule, it exhibits high reactivity, and could be used to replace for highly toxic phosgene as carbonylating agent and for dimethyl sulfate as methylating agent. DMC can be used as raw material to directly synthesize food additives, antioxidants, plant protection agents, high performance resins, fuels, pharmaceutical intermediates, surfactants, etc., thus it is praised as a potential "novel base block" in organic synthesis. Furthermore, since DMC possesses relatively high oxygen content as well as suitable vapor pressure, water resistance and mixing distribution coefficient, it could serve as an ideal gasoline additive. This further extension of the application of the DMC will surely make DMC a new economic growing point in the chemical industry, and is of practical significance due to huge potential demands to DMC.

DMC was mainly synthesized by phosgene method in conventional method. High toxicity of raw material phosgene and corrosiveness of chlorine ion limited the large-scale production and application of DMC. In 1983, Enichem Company in Italy developed a non-phosgene method to synthesize DMC by oxidative carbonylation of methanol in liquid phase [Romano U., Tesei R., Mauri M. M. et al, Synthesis of dimethyl carbonate from methanol, carbon monoxide, and oxygen catalyzed by copper compounds, *Ind. Eng. Chem. Prod. Res. Rev.*, 1980, 19: 396-403; Micheal A. P., Christopher L. M., Review of Dimethyl Carbonate (DMC): Manufacture and its Characteristics as a Fuel Additive. *Energy and Fuels* 1997, 11, 2-29], which brought the synthesis of DMC to a new stage. In 1992, UBE Industries Ltd. in Japan developed a method of gas-phase oxidative carbonylation of methanol [J. Kizlink, Collect. Czech. Chem. Comm. 1993, 58, 1399; Y. Sasaki, Chem. Lett., 1996, 825; S. T. King, Reaction mechanism of oxidative carbonylation of methanol to dimethyl carbonate in Cu—Y zeolite, J. Catal. 1996, 161, 530-538], and this made the synthesis of DMC quickly commercialized. However, since the catalyst used in said method comprises CuCl as main active component, the catalyst has strong corrosion to facilities and short life, and the method suffers expensive raw material gas and toxicity of CO. Another non-phosgene method for preparing DMC is called transesterification method [Knifton J. F., Duranleau R. G., Ethylene glycol-dimethyl carbonate cogeneration, *J. Mol. Catal.*, 1991, 67: 389-399; Nishihara K., U.S. Pat. No. 5,292,917, 1993; Tatsumi T., Watanabe Y. and Koyano K. A., Synthesis of dimethyl carbonate from ethylene carbonate and methanol using TS-1 as solid base catalyst., *Chem. Commun.* 1996(19): 2281-2282], wherein $CO_2$ reacts with ethylene oxide or propylene oxide in the presence of a catalyst to form ethylene carbonate or propylene carbonate, and then ethylene carbonate or propylene carbonate is subjected to transesterifying with methanol to form DMC and ethylene glycol or propylene glycol. In comparison with other synthetic methods, this process has the advantages of cheaper raw materials, lower toxicity of raw materials, no three wastes, high yield, and low corrosion, and the by-product, ethylene glycol or propylene glycol, can be recovered. However, this method has at present the disadvantages that the catalyst used has lower activity and shorter life, reaction conditions are severe, and organic solvents are used during the reaction so that the subsequent separation of the products is difficulty and thus facility investment as well as energy consumption is increased. Therefore researching and developing new reaction approach to further raise technological economical efficiency and technological operability will be of importance.

In order to overcome the above-mentioned disadvantages, the present inventors have developed a novel process and a novel technique for the direct synthesis of DMC from urea and methanol, as disclosed in Chinese Patent Application No. 01130478.2 entitled "Method for preparation of dimethyl carbonate from urea and methanol" and in Chinese Patent Application No. 01131680.2 entitled "Method for preparation of dimethyl carbonate from urea and methanol using heterogeneous catalyst". In such a method, since the raw materials, urea and methanol, are common chemical raw materials, their prices are rather low, and thus raw material cost is lower. In addition, the method has other advantages such as safe and simple process, higher activity of reaction and higher selectivity of the product, and thus could significantly lower the production cost of DMC. However DMC yield of said process is still a little lower and needs further improvement.

DISCLOSURE OF THE INVENTION

The object of the invention is to provide a high conversion and high selectivity supported catalyst for direct synthesis of DMC from urea and methanol, a method for preparing the catalyst, and use of the catalyst.

The catalyst of the present invention has a composition on weight base as follows:
  active component: from 20 to 50 wt %; and
  carrier: from 80 to 50 wt %.

Materials that could be used as the carrier include, but are not limited to, active carbon, α-alumina, γ-alumina, silica, molecular sieve, and the like.

Active component is selected from the group consisting of oxides and chlorides of alkali metals, alkali-earth metals and transition elements, and mixture thereof.

The alkali metals include K, Na, Cs and Li.

The alkali-earth metals include Ca and Mg.

The transition elements include Zn, Pb, Mn, La and Ce.

The catalyst of the present invention can be prepared by a method comprising the steps of:
  preparing an aqueous solution of soluble salt(s) of alkali metal, alkali-earth metal, or transition element according to the composition of the catalyst on weight base;
  adjusting pH value of the solution to 0-5 by KOH or $NH_3 \cdot H_2O$ etc.;
  spraying and impregnating the aqueous solution on a carrier by equal-volume spraying and impregnating process, to prepare an active component-supported carrier;

drying the active component-supported carrier at a temperature of from 100° C. to 250° C. for 2 to 24 hrs; and finally calcining the dried active component-supported carrier at a temperature of from 500° C. to 1000° C. for 2 to 12 hrs.

Useful soluble metal salts include nitrates, acetates, oxalates, hydroxides, halides and the like of alkali metals, alkali-earth metals, and transition elements.

The pH value is preferably adjusted to 1-3.

The calcination temperature is preferably in a range of from 650° C. to 850° C.

The calcination time is preferably in a range of from 3 to 8 hrs.

In the course of the preparation of the catalyst, control of pH value of the aqueous solution, calcination temperature and calcination time are the key points.

The catalytic reaction according to the present invention can be carried out in a catalytic rectification reactor with the catalyst loaded in the reaction section of the catalytic rectification reactor. Methanol solution of urea formed by dissolving urea in methanol enters the catalyst bed layer from the upper portion of the catalyst section, with urea in the solution entering the catalyst bed layer while methanol in the solution entering the rectifying section of the catalytic rectification reactor due to higher temperature. The reaction raw material methanol enters catalyst bed layer from the lower portion of the catalyst section. Urea and the reaction raw material methanol react in the catalyst section to form DMC.

In a preferred embodiment, the catalyst according to the invention is used in the catalytic rectification reactor in a method comprising:

(1) dissolving urea in methanol to form a methanol solution of urea, in which weight percentage of urea is in a range of from 1% to 99%;

(2) feeding the methanol solution of urea into the catalyst bed layer from upper portion of the catalyst section of the catalytic rectification reactor in a feeding rate of from 0.01 to 10 ml/gcat•min, and feeding reaction raw material methanol into the catalyst bed layer from lower portion of the catalyst section of the catalytic rectification reactor in a feeding rate of from 0.01 to 20 ml/gcat•min, wherein the reaction is carried out at conditions including reaction temperature of from 120° C. to 250° C., reaction pressure of from 0.1 MPa to 5 MPa, kettle bottom temperature of from 70° C. to 210° C., stripping section temperature of from 70° C. to 250° C., rectifying section temperature of from 70° C. to 280° C., and reflux ratio of from 1:1 to 20:1.

The weight percentage of urea in the methanol solution of urea is preferably in a range of from 20% to 50%.

The feeding rate of the methanol solution of urea is preferably in a range of from 0.1 to 2 ml/gcat•min.

The feeding rate of the reaction raw material methanol is preferably in a range of from 0.1 to 10 ml/gcat•min.

The reaction temperature is preferably in a range of from 150° C. to 200° C.

The reaction pressure is preferably in a range of from 0.5 MPa to 3 MPa.

The kettle bottom temperature is preferably in a range of from 110° C. to 180° C.

The stripping section temperature is preferably in a range of from 150° C. to 190° C.

The rectifying section temperature is preferably in a range of from 150° C. to 200° C.

The reflux ratio is preferably in a range of from 1:1 to 6:1.

The present invention has the following advantages:

The catalyst according to the present invention is a supported solid catalyst system, and the preparation of the catalyst is simple and has good repeatability so that industrial scale production can be easily achieved; reaction involving catalyst and reactants is of multi-phase catalytic reaction, and thus there is no need to separate catalyst from product; the novel supported catalyst prepared could further enhance the yield of DMC in the catalytic rectification reactor, and possesses higher reactivity and selectivity; and by-product is less.

EMBODIMENTS

Comparative Example

Using ZnO as Catalyst (Catalyst was Obtained by Calcination of ZnO)

60.08 g of urea was dissolved in 602.7 g of methanol to form a methanol solution of urea. Feeding rate of the methanol solution of urea was 0.1 ml/gcat.•min, and feeding rate of methanol was 0.5 ml/gcat.•min. The reaction temperature was 200° C., the reaction pressure was 4.0 MPa, kettle bottom temperature was 170° C., stripping section temperature was 200° C., rectifying section temperature was 200° C., and the reflux ratio was 8:1. Results obtained were shown in Table 1.

Example 1

100 ml of 80 wt % aqueous solution of calcium nitrate was prepared, and its pH value was adjusted to 1.5 by KOH. Said calcium nitrate solution was sprayed and impregnated on 100 g of active carbon carrier by equal-volume spraying and impregnating process, and the carrier with active component supported thereon was then dried at 150° C. for 12 hrs and calcined at 700° C. for 6 hrs. The catalyst thus prepared had a composition of: calcium oxide 21 wt %; and active carbon 79 wt %.

60.08 g of urea was dissolved in 60.12 g of methanol to form a methanol solution of urea. The methanol solution of urea was fed into catalyst bed layer from upper portion of the catalyst section of the catalytic rectification reactor in a feeding rate of 0.1 ml/gcat.•min, and the reaction raw material methanol was fed into the catalyst bed layer from the lower portion of the catalyst section of the catalytic rectification reactor in a feeding rate of 0.5 ml/gcat.•min. The reaction temperature was 150° C., the reaction pressure was 0.2 MPa, kettle bottom temperature was 80° C., stripping section temperature was 85° C., rectifying section temperature was 85° C., and the reflux ratio was 1:1. Results obtained were shown in Table 1.

Example 2

100 ml of 60 wt % aqueous solution of zinc acetate was prepared, and its pH value was adjusted to 1.0 by KOH. Said zinc acetate solution was sprayed and impregnated on 70 g of $SiO_2$ carrier for 1 hr by equal-volume spraying and impregnating process, and the carrier with active component supported thereon was then dried at 250° C. for 10 hrs and calcined at 500° C. for 12 hrs. The catalyst thus prepared had a composition of: zinc oxide 24 wt %, and $SiO_2$ 76 wt %.

60 g of urea was dissolved in 120.13 g of methanol. The methanol solution of urea was fed into catalyst bed layer from upper portion of the catalyst section of the catalytic rectification reactor in a feeding rate of 1 ml/gcat.•min, and the reaction raw material methanol was fed into the catalyst bed layer from the lower portion of the catalyst section of the catalytic rectification reactor in a feeding rate of 5 ml/gcat.•min. The reaction temperature was 170° C., the reaction pressure was 2.0 MPa, kettle bottom temperature was 130° C., stripping section temperature was 170° C., rectifying section temperature was 180° C., and the reflux ratio was 2:1. Results obtained were shown in Table 1.

Example 3

100 ml of 92 wt % aqueous solution of zinc acetate was prepared, and its pH value was adjusted to 2.0 by KOH. Said zinc acetate solution was sprayed and impregnated on 50 g of $SiO_2$ carrier for 1 hr by equal-volume spraying and impregnating process, and the carrier with active component supported thereon was then dried at 150° C. for 10 hrs and calcined at 800° C. for 12 hrs. The catalyst thus prepared had a composition of: zinc oxide 41 wt %, and $SiO_2$ 59 wt %.

60 g of urea was dissolved in 120.13 g of methanol. The methanol solution of urea was fed into catalyst bed layer from upper portion of the catalyst section of the catalytic rectification reactor in a feeding rate of 1 ml/gcat.•min, and the reaction raw material methanol was fed into the catalyst bed layer from the lower portion of the catalyst section of the catalytic rectification reactor in a feeding rate of 2 ml/gcat.•min. The reaction temperature was 170° C., the reaction pressure was 2.0 MPa, kettle bottom temperature was 130° C., stripping section temperature was 170° C., rectifying section temperature was 180° C., and the reflux ratio was 2:1. Results obtained were shown in Table 1.

Example 4

100 ml of 60 wt % aqueous solution of potassium nitrate was prepared, and its pH value was adjusted to 1.2 by KOH. Said potassium nitrate solution was sprayed and impregnated on 70 g of $SiO_2$ carrier for 1 hr by equal-volume spraying and impregnating process, and the carrier with active component supported thereon was then dried at 150° C. for 10 hrs and calcined at 800° C. for 12 hrs. The catalyst thus prepared had a composition of: potassium oxide 22 wt %, and $SiO_2$ 78 wt %.

60 g of urea was dissolved in 120.13 g of methanol. The methanol solution of urea was fed into catalyst bed layer from upper portion of the catalyst section of the catalytic rectification reactor in a feeding rate of 1 ml/gcat.•min, and the reaction raw material methanol was fed into the catalyst bed layer from the lower portion of the catalyst section of the catalytic rectification reactor in a feeding rate of 5 ml/gcat.•min. The reaction temperature was 220° C., the reaction pressure was 2.5 MPa, kettle bottom temperature was 180° C., stripping section temperature was 185° C., rectifying section temperature was 220° C., and the reflux ratio was 2:1. Results obtained were shown in Table 1.

Example 5

100 ml of 40 wt % aqueous solution of cesium nitrate was prepared, and its pH value was adjusted to 3.5 by KOH. Said cesium nitrate solution was sprayed and impregnated on 70 g of $SiO_2$ carrier for 1 hr by equal-volume spraying and impregnating process, and the carrier with active component supported thereon was then dried at 180° C. for 10 hrs and calcined at 800° C. for 12 hrs. The catalyst thus prepared had a composition of: cesium oxide 25 wt %, and $SiO_2$ 75 wt %.

30 g of urea was dissolved in 120.13 g of methanol. The methanol solution of urea was fed into catalyst bed layer from upper portion of the catalyst section of the catalytic rectification reactor in a feeding rate of 1 ml/gcat.•min, and the reaction raw material methanol was fed into the catalyst bed layer from the lower portion of the catalyst section of the catalytic rectification reactor in a feeding rate of 5 ml/gcat.•min. The reaction temperature was 190° C., the reaction pressure was 2.0 MPa, kettle bottom temperature was 130° C., stripping section temperature was 180° C., rectifying section temperature was 190° C., and the reflux ratio was 4:1. Results obtained were shown in Table 1.

Example 6

100 ml of an aqueous solution containing 2 wt % of potassium oxalate and 85 wt % of zinc nitrate was prepared, and its pH value was adjusted to 2.0 by KOH. Said solution was sprayed and impregnated on 50 g of γ-alumina carrier for 2 hrs by equal-volume spraying and impregnating process, and the carrier with active component supported thereon was then dried at 100° C. for 15 hrs and calcined at 750° C. for 4 hrs. The catalyst thus prepared had a composition of: potassium oxide 5 wt %, zinc oxide 40 wt %, and alumina 55 wt %.

60.08 g of urea was dissolved in 320.7 g of methanol. The methanol solution of urea was fed into catalyst bed layer from upper portion of the catalyst section of the catalytic rectification reactor in a feeding rate of 3.5 ml/gcat.•min, and the reaction raw material methanol was fed into the catalyst bed layer from the lower portion of the catalyst section of the catalytic rectification reactor in a feeding rate of 9 ml/gcat.•min. The reaction temperature was 180° C., the reaction pressure was 2.0 MPa, kettle bottom temperature was 180° C., stripping section temperature was 180° C., rectifying section temperature was 180° C., and the reflux ratio was 4:1. Results obtained were shown in Table 1.

Example 7

50 ml of 2 wt % potassium nitrate aqueous solution and 50 ml of 80 wt % zinc nitrate aqueous solution were prepared, and their pH values were adjusted to 2.0 by KOH. Said solutions were sprayed and impregnated on γ-alumina carrier for 1 hr by equal-volume spraying and impregnating process, respectively, and the carrier with active component supported thereon was then dried at 150° C. for 8 hrs and calcined at 800° C. for 8 hrs. The catalyst thus prepared had a composition of: potassium oxide 2 wt %, zinc oxide 31 wt %, and $Al_2O_3$ 67 wt %.

60.08 g of urea was dissolved in 60.7 g of methanol. The methanol solution of urea was fed into catalyst bed layer from upper portion of the catalyst section of the catalytic rectification reactor in a feeding rate of 0.5 ml/gcat.•min, and the reaction raw material methanol was fed into the catalyst bed layer from the lower portion of the catalyst section of the catalytic rectification reactor in a feeding rate of 1.5 ml/gcat.•min. The reaction temperature was 200° C., the reaction pressure was 2.0 MPa, kettle bottom temperature was 170° C., stripping section temperature was 200° C., rectifying section temperature was 200° C., and the reflux ratio was 8:1. Results obtained were shown in Table 1.

Example 8

25 ml of 5 wt % potassium nitrate aqueous solution was prepared and its pH value was adjusted to 4.0 by KOH, while 75 ml of 80 wt % calcium nitrate aqueous solution was prepared and its pH value was adjusted to 2.0. Said solutions were sprayed and impregnated on α-alumina carrier for 2 hrs by equal-volume spraying and impregnating process, respectively, and the carrier with active component supported thereon was then dried at 170° C. for 10 hrs and calcined at 700° C. for 6 hrs. The catalyst thus prepared had a composition of: potassium oxide 2 wt %, zinc oxide 35 wt %, and $Al_2O_3$ 63 wt %.

60.08 g of urea was dissolved in 20.07 g of methanol. The methanol solution of urea was fed into catalyst bed layer from upper portion of the catalyst section of the catalytic rectification reactor in a feeding rate of 2 ml/gcat.•min, and the reaction raw material methanol was fed into the catalyst bed layer from the lower portion of the catalyst section of the catalytic rectification reactor in a feeding rate of 5 ml/gcat.•min. The reaction temperature was 200° C., the reaction pressure was 4.0 MPa, kettle bottom temperature was 170° C., stripping section temperature was 200° C., rectifying section temperature was 200° C., and the reflux ratio was 8:1. Results obtained were shown in Table 1.

Example 9

25 ml of 5 wt % cesium nitrate aqueous solution was prepared and its pH value was adjusted to 5.0 by KOH, while 75 ml of 60 wt % calcium nitrate aqueous solution was prepared and its pH value was adjusted to 2.0. Said solutions were sprayed and impregnated on 50 g of α-alumina carrier for 2 hrs by equal-volume spraying and impregnating process, respectively, and the carrier with active component supported thereon was then dried at 170° C. for 10 hrs and calcined at 650° C. for 6 hrs. The catalyst thus prepared had a composition of: cesium oxide 3 wt %, calcium oxide 22 wt %, and $Al_2O_3$ 75 wt %.

60.08 g of urea was dissolved in 72.7 g of methanol. The methanol solution of urea was fed into catalyst bed layer from upper portion of the catalyst section of the catalytic rectification reactor in a feeding rate of 1.0 ml/gcat.•min, and the reaction raw material methanol was fed into the catalyst bed layer from the lower portion of the catalyst section of the catalytic rectification reactor in a feeding rate of 4.0 ml/gcat.•min. The reaction temperature was 200° C., the reaction pressure was 1.0 MPa, kettle bottom temperature was 170° C., stripping section temperature was 200° C., rectifying section temperature was 200° C., and the reflux ratio was 8:1. Results obtained were shown in Table 1.

Example 10

5 ml of 35 wt % lanthanum nitrate aqueous solution was prepared and its pH value was adjusted to 4.0 by KOH, while 95 ml of 70 wt % zinc nitrate aqueous solution was prepared and its pH value was adjusted to 2.0 by KOH or NH3.H2O. Said solutions were sprayed and impregnated on 70 g of active carbon carrier for 1 hr by equal-volume spraying and impregnating process, respectively, and the carrier with active component supported thereon was then dried at 150° C. for 8 hrs and calcined at 700° C. for 3 hrs. The catalyst thus prepared had a composition of: lanthanum oxide 2 wt %, zinc oxide 28 wt %, and active carbon 70 wt %.

174.96 g of urea was dissolved in 29.7 g of methanol. The methanol solution of urea was fed into catalyst bed layer from upper portion of the catalyst section of the catalytic rectification reactor in a feeding rate of 2 ml/gcat.•min, and the reaction raw material methanol was fed into the catalyst bed layer from the lower portion of the catalyst section of the catalytic rectification reactor in a feeding rate of 5 ml/gcat.•min. The reaction temperature was 200° C., the reaction pressure was 1.5 MPa, kettle bottom temperature was 200° C., stripping section temperature was 200° C., rectifying section temperature was 200° C., and the reflux ratio was 10:1. Results obtained were shown in Table 1.

Example 11

100 ml of 70 wt % magnesium hydroxide aqueous solution was prepared, and its pH value was adjusted to 1.5 by KOH. Said solution was sprayed and impregnated on 70 g of molecular sieve carrier for 1 hr by equal-volume spraying and impregnating process, and the carrier with active component supported thereon was then dried at 150° C. for 8 hrs and calcined at 650° C. for 3 hrs. The catalyst thus prepared had a composition of: magnesium oxide 30 wt %, and molecular sieve 70 wt %.

74.96 g of urea was dissolved in 459.7 g of methanol to form a solution. The methanol solution of urea was fed into catalyst bed layer from upper portion of the catalyst section of the catalytic rectification reactor in a feeding rate of 1 ml/gcat.•min, and the reaction raw material methanol was fed into the catalyst bed layer from the lower portion of the catalyst section of the catalytic rectification reactor in a feeding rate of 3 ml/gcat.•min. The reaction temperature was 200° C., the reaction pressure was 2.0 MPa, kettle bottom temperature was 200° C., stripping section temperature was 200° C., rectifying section temperature was 200° C., and the reflux ratio was 4:1. Results obtained were shown in Table 1.

Example 12

10 ml of 20 wt % aqueous solution of potassium nitrate was prepared and its pH value was adjusted to 3.0 by KOH. 10 ml of 35 wt % aqueous solution of lanthanum nitrate and 80 ml of 80 wt % aqueous solution of zinc nitrate were prepared and their pH value were adjusted to 2.0. Said solutions were sprayed and impregnated on 70 g of γ-alumina carrier for 1 hr by equal-volume spraying and impregnating process, and the carrier with active component supported thereon was then dried at 150° C. for 8 hrs and calcined at 700° C. for 3 hrs. The catalyst thus prepared had a composition of: potassium oxide 2 wt %, lanthanum oxide 2 wt %, zinc oxide 27 wt %, and $Al_2O_3$ 69 wt %.

74.96 g of urea was dissolved in 459.7 g of methanol to form a solution. The methanol solution of urea was fed into catalyst bed layer from upper portion of the catalyst section of the catalytic rectification reactor in a feeding rate of 10 ml/gcat.•min, and the reaction raw material methanol was fed into the catalyst bed layer from the lower portion of the catalyst section of the catalytic rectification reactor in a feeding rate of 20 ml/gcat.•min. The reaction temperature was 200° C., the reaction pressure was 1.5 MPa, kettle bottom temperature was 200° C., stripping section temperature was 200° C., rectifying section temperature was 200° C., and the reflux ratio was 10:1. Results obtained were shown in Table 1.

Example 13

100 ml of 70 wt % magnesium chloride aqueous solution was prepared and its pH value was adjusted to 1.5 by KOH. Said solution was sprayed and impregnated on 60 g of molecular sieve carrier for 1 hr by equal-volume spraying and impregnating process, and the carrier with active component supported thereon was then dried at 150° C. for 8 hrs and calcined at 950° C. for 2 hrs. The catalyst thus prepared had a composition of: magnesium chloride 50 wt %, and molecular sieve 50 wt %.

74.96 g of urea was dissolved in 459.7 g of methanol to form a solution. The methanol solution of urea was fed into catalyst bed layer from upper portion of the catalyst section of the catalytic rectification reactor in a feeding rate of 1 ml/gcat.•min, and the reaction raw material methanol was fed into the catalyst bed layer from the lower portion of the catalyst section of the catalytic rectification reactor in a feeding rate of 3 ml/gcat.•min. The reaction temperature was 200° C., the reaction pressure was 2.0 MPa, kettle bottom temperature was 200° C., stripping section temperature was 200° C., rectifying section temperature was 200° C., and the reflux ratio was 4:1. Results obtained were shown in Table 1.

Example 14

100 ml of 70 wt % lead nitrate aqueous solution was prepared and its pH value was adjusted to 0.5 by KOH. Said solution was sprayed and impregnated on 60 g of molecular sieve carrier for 1 hr by equal-volume spraying and impregnating process, and the carrier with active component supported thereon was then dried at 150° C. for 10 hrs and calcined at 750° C. for 10 hrs. The catalyst thus prepared had a composition of: lead oxide 36 wt %, and molecular sieve 64 wt %.

74.96 g of urea was dissolved in 459.7 g of methanol to form a solution. The methanol solution of urea was fed into catalyst bed layer from upper portion of the catalyst section of the catalytic rectification reactor in a feeding rate of 0.2 ml/gcat.•min, and the reaction raw material methanol was fed into the catalyst bed layer from the lower portion of the catalyst section of the catalytic rectification reactor in a feeding rate of 0.8 ml/gcat.•min. The reaction temperature was 185° C., the reaction pressure was 1.0 MPa, kettle bottom temperature was 120° C., stripping section temperature was 170° C., rectifying section temperature was 185° C., and the reflux ratio was 4:1. Results obtained were shown in Table 1.

Example 15

100 ml of 60 wt % sodium nitrate aqueous solution was prepared and its pH value was adjusted to 3.5 by KOH. Said solution was sprayed and impregnated on 70 g of silica carrier for 1 hr by equal-volume spraying and impregnating process, and the carrier with active component supported thereon was then dried at 180° C. for 10 hrs and calcined at 800° C. for 12 hrs. The catalyst thus prepared had a composition of: sodium oxide 25 wt %, and $SiO_2$ 75 wt %.

30 g of urea was dissolved in 120.13 g of methanol to form a solution. The methanol solution of urea was fed into catalyst bed layer from upper portion of the catalyst section of the catalytic rectification reactor in a feeding rate of 1 ml/gcat.•min, and the reaction raw material methanol was fed into the catalyst bed layer from the lower portion of the catalyst section of the catalytic rectification reactor in a feeding rate of 5 ml/gcat.•min. The reaction temperature was 190° C., the reaction pressure was 2.0 MPa, kettle bottom temperature was 130° C., stripping section temperature was 180° C., rectifying section temperature was 190° C., and the reflux ratio was 4:1. Results obtained were shown in Table 1.

TABLE 1

| | Results of the reaction | |
|---|---|---|
| | Conversion of urea % | DMC yield % |
| ve Example | 96.89 | 49.73 |
| Example 1 | 98.50 | 58.91 |
| Example 2 | 97.62 | 53.56 |
| Example 3 | 99.66 | 68.56 |
| Example 4 | 97.24 | 58.12 |
| Example 5 | 98.75 | 59.42 |
| Example 6 | 100.00 | 62.98 |
| Example 7 | 100.00 | 76.88 |
| Example 8 | 100.00 | 74.92 |
| Example 9 | 99.12 | 64.75 |
| Example 10 | 98.54 | 75.68 |
| Example 11 | 98.54 | 55.65 |
| Example 12 | 98.98 | 70.29 |
| Example 13 | 98.12 | 52.48 |
| Example 14 | 99.89 | 62.68 |
| Example 15 | 98.18 | 52.35 |

What is claimed is:

1. A method for preparing a catalyst comprising the steps of:
    preparing an aqueous solution of soluble salt(s) of K, Na, Cs, Li, Ca, Mg, Zn, Pb, Mn, La or Ce;
    adjusting pH value of the solution to 0-5;
    spraying and impregnating the aqueous solution on the carrier by equal-volume spraying and impregnating process, to prepare an active component-supported carrier;
    drying the active component-supported carrier at a temperature of from 100° C. to 250° C. for 2 to 24 hrs; and
    the active component-supported carrier at a temperature from 500° C. to 1000° C. for 2 to 12 hrs;
    wherein the catalyst comprises:
    20 to 50 wt % of an active component; and
    80 to 50 wt % of a carrier component,
    wherein the carrier component comprises at least one carrier selected from the group consisting of active carbon, α-alumina, λ-alumina, silica, and molecular sieve; and wherein the active component comprises one or more active component selected from the group consisting of oxides and chlorides of K, Na, Cs, Li, Ca, Mg, Zn, Pb, Mn, La or Ce.

2. The method according to claim 1, characterized in that the soluble salt(s) is/are selected from the group consisting of nitrates, acetates, oxalates, hydroxides and halides of K, Na, Cs, Li, Ca, Mg, Zn, Pb, Mn, La, and Ce.

3. The method according to claim 1, characterized in that the pH value is in a range of from 1 to 3.

4. The method according to claim 1, characterized in that the calcination temperature is in a range of from 650 to 850° C.

5. The method according to claim 1, characterized in that the calcination time is in a range of from 3 to 8 hours.

* * * * *

UNITED STATES PATENT AND TRADEMARK OFFICE
CERTIFICATE OF CORRECTION

| | |
|---|---|
| PATENT NO. | : 7,271,120 B2 |
| APPLICATION NO. | : 11/209052 |
| DATED | : September 18, 2007 |
| INVENTOR(S) | : Yuhan Sun et al. |

Page 1 of 1

It is certified that error appears in the above-identified patent and that said Letters Patent is hereby corrected as shown below:

In Claim 1, lines 12-13: should read

--<u>finally calcining the dried</u> [the] active component-supported carrier at a temperature from 500° C. to 1000° C. for 2 to 12 hrs;--

Signed and Sealed this

Twentieth Day of November, 2007

JON W. DUDAS
*Director of the United States Patent and Trademark Office*